United States Patent [19]

Wakamatsu et al.

[11] Patent Number: 4,835,303

[45] Date of Patent: * May 30, 1989

[54] PROCESS FOR PRODUCING DRY α-L-ASPARTYL-L-PHENYLALANINE METHYL ESTER

[75] Inventors: Hideotoshi Wakamatsu, Shin-nanyo; Shigeaki Irino, Yamaguchi; Tsuneo Harada; Akira Tokuda, both of Shin-nanyo; Kiyotaka Oyama, Hikari, all of Japan

[73] Assignee: Toyo Soda Manufacturing Company, Ltd., Yamaguchi, Japan

[*] Notice: The portion of the term of this patent subsequent to Mar. 7, 2006 has been disclaimed.

[21] Appl. No.: 84,087

[22] Filed: Aug. 11, 1987

[30] Foreign Application Priority Data

Aug. 12, 1986 [JP] Japan ................................ 61-187758
Aug. 13, 1986 [JP] Japan ................................ 61-188662

[51] Int. Cl.$^4$ ........................................... C07C 103/52
[52] U.S. Cl. ..................................................... 560/41
[58] Field of Search ........................ 560/41; 530/801; 426/548; 34/10, 16, 31

[56] References Cited

U.S. PATENT DOCUMENTS 4,579,747 4/1986 Sugiyama et al. .................. 426/548

FOREIGN PATENT DOCUMENTS 42623 4/1982 Japan .
95862 6/1984 Japan .
172444 9/1984 Japan .
37949 2/1985 Japan .

OTHER PUBLICATIONS

Perry et al., Chemical Engineers' Handbook, 5th ed., McGraw-Hill, N.Y., pp. 20-4 to 20-16 (1973).
"Application Potential for Aspartame in Low Calorie and Dietetic Foods, In Low Calorie and Special Dietary Foods", pp. 59-114, CRC Press 1978, CFR 21, Food and Drugs Revised as of Apr. 1, 1981.

Primary Examiner—Bruce D. Gray
Attorney, Agent, or Firm—Nixon & Vanderhye

[57] ABSTRACT

A process for producing dry α-L-aspartyl-L-phenylalanine methyl ester, which comprises drying wet crystals of α-L-aspartyl-L-phenylalanine methyl ester by means of an air having an absolute humidity of at least 0.015 kg/kg or at most 0.01 kg/kg.

8 Claims, No Drawings

PROCESS FOR PRODUCING DRY α-L-ASPARTYL-L-PHENYLALANINE METHYL ESTER

The present invention relates to a process for producing α-L-aspartyl-L-phenylalanine methyl ester (hereinafter referred to as Aspartame) having excellent storage stability or an improved solubility.

Aspartame has two types of crystal forms i.e. I and II types. The I type crystals are hygroscopic, and they are likely to undergo color change or decomposition during storage. Whereas, the II type crystals are less hygroscopic, and they are believed to have good flowability and storage stability.

Heretofore, a method has been proposed wherein wet Aspartame crystals are dried at a temperature of at least 80° C. to obtain the II type crystals of Aspartame (Japanese Unexamimed Patent Publications No. 172441/1984 and No. 37949/1985), or a method for preparing granules has been known in which dried II type crystals are hydrated to have a water content of from 35 to 45% by weight, followed by extrusion granulation and drying again (Japanese Unexamined Patent Publication No. 95862/1984).

In the conventional processes, crystals are dried at a high temperature to obtain the II type crystals, and it is likely that a decomposition product of Aspartame i.e. a diketopiperadine derivative, forms. Further, in order to obtain granules, a dried product of the II type crystals of Aspartame is required to be hydrated once, followed by granulation and drying again, such being disadvantageous from the viewpoint of the process control and costs for energy.

On the other hand, various methods have been proposed to obtain Aspartame having an excellent solubility. For example, it has been proposed to granulate Aspartame together with an excipient having an excellent solubility, to form it into disintegrating tablets in combination with an excipient and a disintegrator, or to form it into effervescing tablets in combination with an effervescing agent and a neutralizing agent. Another method is known wherein a specific amount of water is added to Aspartame II type crystals, followed by mixing, granulating and drying (Japanese Unexamined Patent Publication No. 95862/1984). As mentioned above, Aspartame II type crystals have a low hygroscopicity and an excellent storage stability, as compared with the I type crystals. Therefore, the process for producing Aspartame II type crystals have been extensively studied. However, no substantial studies have been made on Aspartame I type crystals.

Aspartame has poor dispersibility and solubility in water. In its application to food, Aspartame is likely to form agglomerates due to the poor dispersibility and solubility when dissolved, which make the operation of dissolving it in water difficult and time-consuming.

In conventional methods, it is necessary to dissolve Aspartame in water or to form it into a slurry once. Therefore, there are problems with respect to the operations, the process control and costs for energy. On the other hand, if other substances are mixed to Aspartame to improve the solubility, the presence of such substances may likely be a problem depending upon a particular use. Therefore, there is strong demand for highly pure Aspartame having an excellent solubility.

According to the studies by the present inventors, of the above-mentioned two types of Aspartame crystals, the I type crystals are far superior in the solubility to the II type crystals. A product obtained by drying wet Aspartame crystals by an industrial method, is usually a mixture of the I and II type crystals. Therefore, it is also an important technical subject to develop an industrial process for the production of the I type crystals containing no or only a small amount of the II type crystals.

It is an object of the present invention to provide a process for producing Aspartame having excellent storage stability without requiring high temperature drying and redrying as required in the conventional processes.

It is another object of the present invention to provide a process for producing Aspartame having an improved solubility without an addition of other substances or without necessity of a step of dissolving or dispersing it in water once.

The present inventors have conducted extensive research to solve the above-mentioned problems, and have found it possible to attain the above objects by controlling the humidity of the air for drying wet Aspartame crystals.

Namely, it has been found that stable II type crystals of Aspartame are obtainable by drying wet Aspartame crystals with an air having an absolute humidity of at least 0.015 kg/kg, whereas I type crystals of Aspartame having an improved solubility are obtainable by drying wet Aspartame crystals with an air having an absolute humidity of at most 0.01 kg/kg.

Thus, the present invention provides a process for producing dry α-L-aspartyl-L-phenylalanine methyl ester, which comprises drying wet crystals of α-L-aspartyl-L-phenylalanine methyl ester by means of an air having an absolute humidity of at least 0.015 kg/kg or at most 0.01 kg/kg.

Now, the present invention will be described in detail with reference to the preferred embodiments.

The wet Aspartame crystals prior to drying in accordance with the process of the present invention may be prepared by any crystallization and separation methods. There is no restriction as to the method for the preparation of the wet Aspartame crystals.

The wet Aspartame crystals thus obtained may or may not be treated by a granulator. When it is treated by a granulator, any type of granulator such as an extrusion type granulator or a compression type granulator may be employed.

Now, the process for the production of stable Aspartame will be described. When the wet Aspartame crystals are treated by extrusion type granulator, granules of a cylindrical shape can be obtained by passing the wet Aspartame crystals through a screen having a mesh size of from 0.1 to 10.0 mm in diameter. It is preferred to pwass the wet crystals through a screen having a mesh size of from 1.0 to 4.0 mm in diameter.

There is no particular restriction as to the temperature and the drying method for the drying of wet Aspartame crystals. However, if the temperature is too high, a diketopiperadine derivative as a decomposition product of Aspartame is likely to form. Therefore, the drying is preferably conducted at a temperature of lower than 80° C. The drying machine may be of a usual type, but is preferably an air stream drier or a fluidized drier whereby the retention time is long. For the production of stable Aspartame, the air used for drying wet Aspartame has an absolute humidity of at least 0.015 kg/kg. In order to obtain stable Aspartame i.e. II type crystals of Aspartame, the partial pressure of the internal stream should preferably be high during the drying operation, and therefore it is preferred to use an air having a humidity as high as possible.

Now, the process for the production of Aspartame having an improved solubility will be described.

When, granules of wet Aspartame having a specific surface area of 4 m²/g or higher is dried, the resulting dried granules will usally be mainly of I type crystals, and when wet Aspartame granules having a specific surface area of less than 4 m²/g is dried, the proportion of II type crystals in the resulting dried granules increases. Whereas, according to the present invention, a dried air having an absolute humidity of at most 0.01 kg/kg is used as a hot air stream during the drying operation, whereby it is possible to obtain a product composed essentially of I type crystals not only when wet Aspartame crystals which are not granulated are used, but also when granulated wet Aspartame crystals, particularly granules having a specific surface ara of less than 4 m²/g, are used.

According to the present invention, there is no particular restriction as to the temperature and other drying conditions. However, Aspartame is not stable at a high temperature, and when it is dried at a high temperature, a part of Aspartame is readily converted to a diketopiperadine derivative. The diketopiperadine derivative is non-toxic and safe, but it lacks in sweetness, thus leading to a loss of overall sweetness. Whereas, the higher the drying temperature, the higher the conversion of Aspartame I type crystals to Aspartame II type crystals. Therefore, Aspartame is dried preferably at a temperature of lower than 80° C.

Any method and device for drying Aspartame may be used in the present invention. A conventional method such as air stream drying in a fixed-bed stream or drying in a fluidized-bed system may be employed.

Now, the present invention will be described in further detail with reference to examples. However, it should be understood that the present invention is by no means restricted to such specific examples.

In the examples, the ratio of I or II type crystals (the ratio (%) of the I or II type crystals to the total amount of the I and II type crystals) was determined as follows:

Standard samples of the I and II type crystals were mixed at various ratios, and calibration curve was prepared based on the ratios in the strength of the specific peaks at the respective X-ray diffraction angles (2φ) of 4.4° (I type) and 5.0° (II type). Then, the ratio of the I or II type crystals was determined by comparing the strength ratio of each sample with the calibration curve.

EXAMPLES 1 TO 6

Wet Aspartame crystals obtained by solid-liquid separation by means of a centrifugal separator, were extruded through a screen having a mesh size of 2.0 mm in diameter, and granulated. The wet granules (60 g) thus obtained were dried in an air stream drier by means of a hot air stream (at a velocity of 1 m/s). The water content and the ratio of II type crystals (%) of dry Aspartame crystals thus obtained, were measured.

The results are shown in Table 1.

TABLE 1

| Number of Example or comparative Example | Temperature for drying (°C.) | Absolute humidity of the hot air stream (kg/kg) | Water content after drying (%) | Ratio of II type crystals (%) |
|---|---|---|---|---|
| Example 1 | 70 | 0.0150 | 1.7 | 70 |
| Example 2 | " | 0.0210 | 1.9 | 81 |
| Example 3 | " | 0.0300 | 2.0 | 98 |
| Comparative Example 1 | " | 0.0083 | 2.1 | 8 |
| Example 4 | 60 | 0.0150 | 1.6 | 71 |
| Example 5 | " | 0.0210 | 2.0 | 78 |
| Example 6 | " | 0.0300 | 2.1 | 91 |
| Comparative Example 2 | " | 0.0083 | 3.1 | 7 |

As is apparent from the foregoing description, according to this embodiment, dry Aspartame II type crystals having excellent storage stability are obtainable, which used to be hardly producible at a temperature of lower than 80° C.

The dry Aspartame product having excellent storage stability of the present invention is particularly useful when it is used as a table sweetener in the form of granules or tablets together with sugars or other substances.

In the following examples, the solubility of Aspartame crystals was determined by measuring the duration till 1 g of Aspartame crystals which was added to 500 ml of distilled water at 20° C. and stirred (by a magnetic stirrer at 200 r.p.m.), was completely dissolved as visually observed.

EXAMPLES 7 TO 11

Wet Aspartame crystals obtained by a solid-liquid separation by means of a centrifugal separator, were extruded through a screen having a mesh size of 2 mm in diameter, and granulated to have a specific surface area of less than 4 m²/g. Then 4.8 kg of wet Aspartame granules thus obtained were dried in a fluidized-bed drier by means of a hot air stream of 70° C. for 120 minutes. Various airs having different humidity levels were used. The results thereby obtained are shown in Table 2.

TABLE 2

| Number of Example or comparative Example | Absolute humidity of the hot air stream (kg/kg) | Final water content (%) | Solubility (min) | Ratio of I type crystals (%) |
|---|---|---|---|---|
| Example 7 | 0.004 | 1.9 | 4–5 | 95 |
| Example 8 | 0.004 | 2.1 | " | 98 |
| Example 9 | 0.008 | 2.5 | " | 97 |
| Example 10 | 0.008 | 2.6 | " | 94 |
| Example 11 | 0.010 | 2.5 | 5–6 | 89 |
| Comparative Example 3 | 0.030 | 2.8 | 17–18 | 28 |

EXAMPLES 12 TO 17

Granulated wet Aspartame crystals (60 g) prepared in the same manner as in Example 7, were dried in the air stream drier by means of a hot air stream at a velocity of 1.0 m/sec). The results are shown in Table 3.

TABLE 3

| Number of Example or comparative Example | Temperature (°C.) | Absolute humidity of the hot air stream (kg/kg) | Final water content (%) | Solubility (min) | Ratio of I type crystals (%) |
|---|---|---|---|---|---|
| Example 12 | 70 | 0.0008 | 0.8 | 5–6 | 98 |

TABLE 3-continued

| Number of Example or comparative Example | Temperature (°C.) | Absolute humidity of the hot air stream (kg/kg) | Final water content (%) | Solubility (min) | Ratio of I type crystals (%) |
| --- | --- | --- | --- | --- | --- |
| Example 13 | " | 0.0042 | 2.0 | 6–7 | 90 |
| Example 14 | " | 0.0083 | 2.1 | 6–7 | 92 |
| Comparative Example 4 | " | 0.0125 | 2.2 | 14–15 | 42 |
| Example 15 | 60 | 0.0008 | 1.7 | 5–6 | 100 |
| Example 16 | " | 0.0042 | 2.9 | 5–6 | 96 |
| Example 17 | " | 0.0083 | 3.1 | 6–7 | 93 |
| Comparative Example 5 | " | 0.0125 | 3.2 | 14–15 | 50 |

As is apparent from the foregoing description, according to this embodiment, it is possible to obtain dry Aspartame having an excellent solubility without disadvantages with respect to the process control and costs for energy, or without necessity of mixing it with other substances. According to this embodiment I type crystals of Aspartame having an excellent solubility are selectively obtainable even when the specific surface area of granulated wet Aspartame is less than 4 $m^2/g$.

The dry Aspartame products of the present invention are widely useful as a sweetener for soft drinks, a table sweetener or a sweetener for other foods.

We claim:

1. A process for producing dry α-L-aspartyl-L-phenylalanine methyl ester, which process comprises the step of drying wet crystals of α-L-aspartyl-phenylalanine methyl ester in air having an absolute humidity of at least 0.015 kg/kg to obtain stable α-L-aspartyl-L-phenylalanine methyl ester crystals in which the ratio of II-type crystals is at least 70%.

2. A process according to claim 1, wherein the drying is conducted at a temperature of lower than 80° C.

3. A process according to claim 1, wherein the drying is conducted under atmospheric pressure.

4. A process according to claim 1, wherein the drying is conducted in a fluidized-bed dryer or in an air stream dryer.

5. A process for producing dry α-L-aspartyl-L-phenylalanine methyl ester, which process comprises the step of drying wet crystals of α-L-aspartyl-L-phenylalanine methyl ester in air having an absolute humidity of at most 0.01 kg/kg to obtain α-L-aspartyl-L-phenylalanine methyl ester with improved solubility and in which the ratio of I-type crystals is at least 89%.

6. A process according to claim 5, wherein the wet crystals of α-L-aspartyl-L-phenylalanine methyl ester are granulated by a granulator into granules having a diameter of from 0.1 to 10.0 mm prior to the drying.

7. A process according to claim 5, wherein the wet crystals of α-L-aspartyl-L-phenylalanine methyl ester are not treated by a granulator.

8. A process according to claim 5, wherein the wet crystals of α-L-aspartyl-L-phenylalanine methyl ester are granulated so that the specific surface area of the granules at the initiation of the drying is less than 4 $m^2/g$.

* * * * *